US00PP15091P2

(12) United States Plant Patent
Whitcomb

(10) Patent No.: US PP15,091 P2
(45) Date of Patent: Aug. 17, 2004

(54) HIBISCUS PLANT NAMED 'WHIT XX'

(50) Latin Name: *Hibiscus moscheutos*
Varietal Denomination: Whit XX

(75) Inventor: Carl Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 12 days.

(21) Appl. No.: 10/693,073

(22) Filed: Oct. 23, 2003

(51) Int. Cl.[7] ..... A01H 5/00
(52) U.S. Cl. ..... Plt./257
(58) Field of Search ..... Plt./257

(56) References Cited

U.S. PATENT DOCUMENTS

PP4,271 P 6/1978 Darby ..... Plt./257
PP10,793 P 2/1999 Fleming ..... Plt./257
PP11,853 P2 5/2001 Fleming ..... Plt./257
PP13,631 P2 3/2003 Fleming ..... Plt./257
PP13,913 P3 6/2003 Fleming ..... Plt./257

*Primary Examiner*—Kent Bell
(74) *Attorney, Agent, or Firm*—Streets & Steele; Jeffrey L. Streets; Frank J. Campigotto

(57) ABSTRACT

A new and distinct cultivar of winter hardy hibiscus named 'Whit XX' is the result of a chance seedling among a seedling population specifically grown for the purpose of screening for variations. This new and distinct cultivar is characterized by being dwarf in stature relative to the species and all other seedlings from the same parent, has blood red flowers that are between about 3.5 and about 6 inches in diameter. The plant is further characterized as having unusually dark green, broadly lanceolate leaves, with a uniform growth habit of dense, stiff branches. Flower production occurs from early July to frost in north central Oklahoma.

4 Drawing Sheets

Genus and species: *Hibiscus moscheutos.*
Varietal denomination: Hardy Hibiscus 'Whit XX'.

BACKGROUND OF THE INVENTION

1. Field of the Invention

This invention relates to a new and distinct variety or cultivar of the herbaceous perennial, *Hibiscus moscheutos,* commonly known as hardy hibiscus or common mallow.

2. Description of the Related Art

Hardy hibiscus is native to wet areas over much of the eastern third of the United States and has been grown as a garden plant since the early settlements. The new and distinct plant of this invention was discovered as a selected seedling whose parent was a single, large, isolated but open pollinated parent that had been growing on the same farmstead in north central Oklahoma for over 30 years. The parent plant was about seven to nine feet tall and produced pink flowers that were about eight to eleven inches in diameter.

The inventor of this new and distinct hardy hibiscus gathered a large quantity of seeds from the parent plant and planted them all. Although only a fraction of the planted seeds germinated, 854 seedlings resulted and were transplanted into rows in a field as part of a breeding program. The new plant of this invention was one of those seedlings and was distinctly different from both the parent plant and its other siblings, being characterized as having a dwarf growth habit, dense, stiff branches, unusually dark green leaves and blood red flowers.

This new and distinct plant has been asexually propagated. Asexual reproduction of the new plant was accomplished by rooting cuttings taken from the original plant in Stillwater, Okla. Each successive reproduction of the new plant by cuttings has shown the unique features that characterize this new hardy hibiscus indicating that the unique features of this plant are stable. Growth, flowering, flower color, foliage color and disease resistance remain constant with the 'Whit XX' cultivar.

SUMMARY OF THE INVENTION

The present invention resulted from the discovery of a new and distinct variety of hibiscus, *Hibiscus moscheutos,* which has been given the cultivar name 'Whit XX'. 'Whit XX' is characterized as being dwarf in stature relative both to the species and to all other seedlings from the same parent. This new variety of hibiscus is further characterized as having blood red flowers having a diameter of between about 3.5 and about six inches and as having unusually dark green, broadly lanceolate leaves. The new variety of hibiscus has a uniform growth habit of dense, stiff branches. Flower production occurs from early July to frost in north central Oklahoma.

BOTANICAL DESCRIPTION OF THE PLANT

Figure 1:
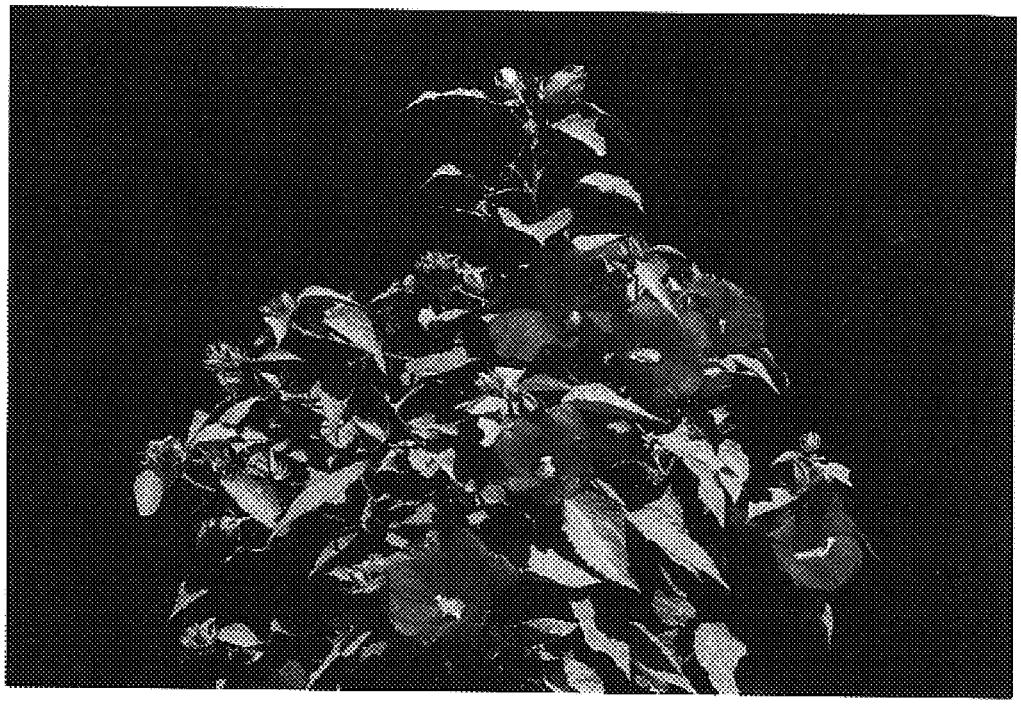
FIG. 1 is a full color photographic view of my new hibiscus plant in full flower in Oklahoma.
Figure 2:
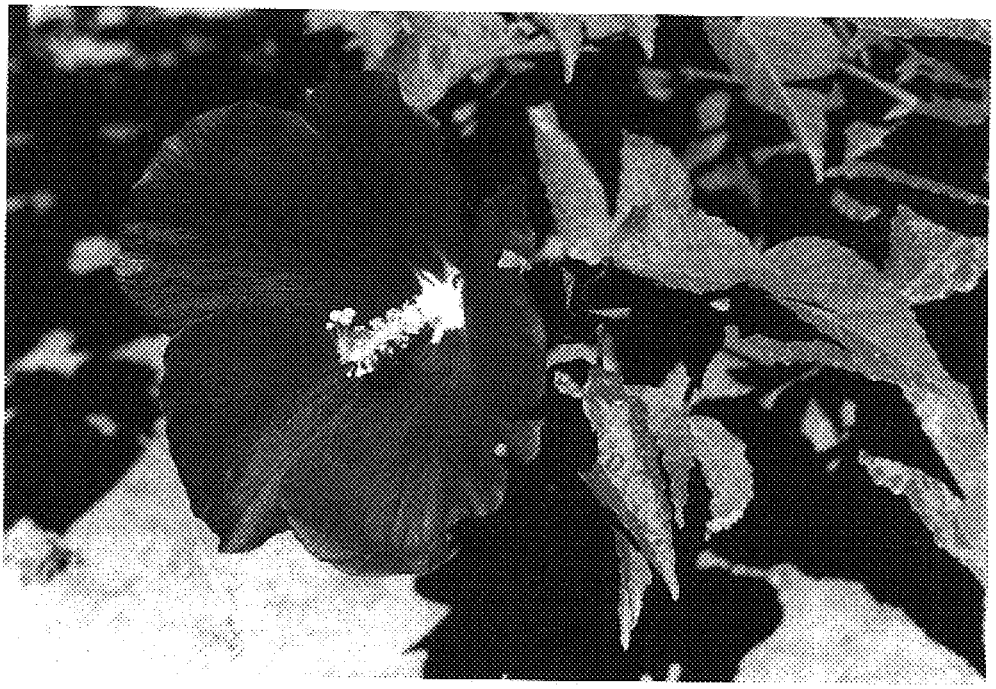
FIG. 2 is a full color photographic view of a flower of the plant shown in FIG. 1.
Figure 3:
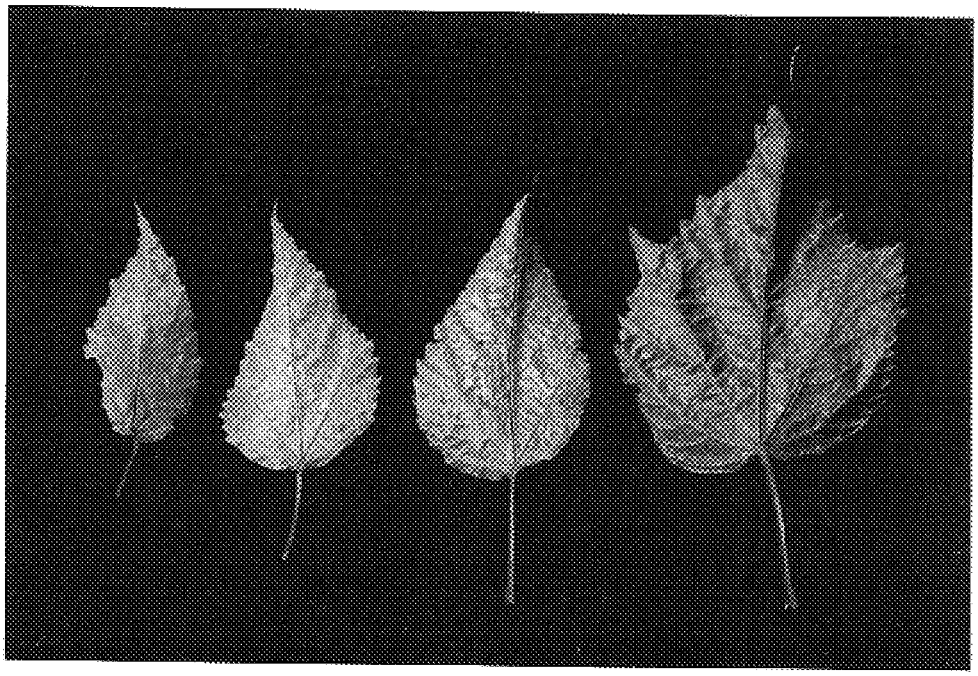
FIG. 3 is a full color photographic view of the range of leaf sizes and shapes found on a typical specimen of my new hardy hibiscus plant.
Figure 4:
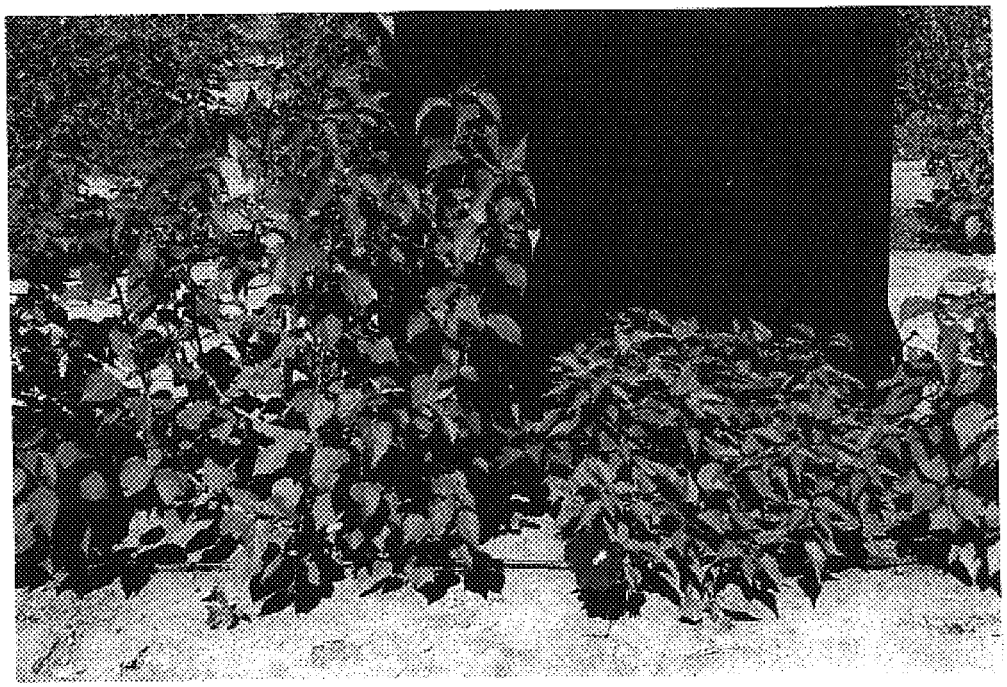
FIG. 4 is a full color photographic view of the original specimen of the present invention, shown in the field for size comparison to typical seedlings from the same parent and of the same age as my new hardy hibiscus plant.

The following botanical description is of the new and distinct cultivar of the hardy hibiscus, *Hibiscus moscheutos,* named 'Whit XX'. Specific color designations set forth by number designations are in accordance with The Royal Horticultural Society Colour Chart. General color recitations are consistent with ordinary American color terminology.

'Whit XX' has not been observed under all possible environmental conditions. It is to be understood that the phenotype may vary significantly with variations in environment such as soils, temperature, light intensity, and length of day, without any difference in the genotype of the plant. The following botanical characteristics and observations are taken from the plant when grown under normal outdoor conditions in north central Oklahoma. The described plant was three years old and was planted in a three gallon container. Plants grown in one gallon or three gallon containers for one year exhibited no change in characteristics.

The plant:

*Type.*—Herbaceous perennial.

*Classification.*—Hardy hibiscus plant, *Hibiscus moscheutos.*

*Origin.*—An open pollination of an unnamed female hibiscus plant and an unknown male hibiscus plant.

*Parentage.*—The parent plant was about seven to nine feet tall and produced pink flowers that were about eight to eleven inches in diameter. The parent plant had a loose, open growth in north central Oklahoma. The parent plant, destroyed in a fire, was an unnamed hibiscus plant.

*Propagation.*—The plant is easy to propagate, with the distinguishing characteristics of each reproduction of the asexually propagated offspring remaining identical to the parent.

*Size and shape.*—The growth habit of the plant forms a dense, low mound. The growth rate is vigorous in late spring to early summer, with very little new growth thereafter. The plant form is characterized as bushy annual growth from perennial roots. In north central Oklahoma, the plant size is characterized as having a height of between about 20 and about 40 inches, with a spread of between about 30 and about 45 inches.

*Hardiness.*—USDA hardiness zones 5 through 9.

*General health and pest susceptibility.*—The plant is very resistant to powdery mildew and other diseases, although minor damage from grasshoppers may occur.

Folliage:

*Arrangement on stems.*—Alternate.

*Shape of leaves.*—Broadly lanceolate. Acuminate to caudate at the tip. Rounded to slightly truncate at the base.

*Size of leaves.*—Variable, with leaf blades ranging from between about 2 and about 6 inches long and from between about 2 and about 4 inches wide.

*Margins of leaves.*—Irregularly crenate.

*Color of leaves.*—The upper surface of young and old leaves is approximately RHS 147-A or B. The primary veins in the upper leaf surface that are in full sun are approximately RHS 187-A. The lower surface of young and old leaves and the primary veins are approximately RHS 191-A or B.

*Surface texture of leaves.*—Rough, variably rugosa.

*Leaf petiole.*—The leaf petiole is between about 1 and about 2.5 inches long. The color, when exposed to full sun, is approximately RHS 182-B. The color when not exposed to full sun is approximately RHS 191-A or B or RHS 152-A or B.

*Stipules.*—None.

*Stems.*—The stems are stout with limited flex. The stem diameters at or near the soil line range from between about 0.5 and about 1.5 inches. Stem growth starts in the spring and extends continuously with no nodes until the plant's full height is reached. Flowering then begins.

*Stem color.*—The color of young stems and old stems in shade is approximately 147-B or C, transitioning to approximately R.H.S. 182-A, B or C when they are exposed to full sun.

Flowers:

*Blooming period.*—The plant blooms from early July to frost in north central Oklahoma.

*Blooming habit.*—Single blooms in the leaf axils. However, there may be one to four blooms at the tip of a branch and from one to twenty or more blooms on a plant at any one time.

*Flower buds.*—The flower buds have a diameter of between about one and about 1.5 inches and a length of between about 1.25 and about 2.5 inches. The color of the calyx is approximately RHS 191-A.

*Flower size, fragrance and lastingness.*—The flowers have a diameter of between about 3.5 and about six inches and have a depth of between about 1 and about 3 inches. The flowers have no fragrance and each flower lasts for one day.

*Flower shape.*—Near flat face with overlapping petals to slightly funnel form.

*Number of petals.*—Most of the flowers have five petals, but occasionally a flower may have four, six or seven petals.

*Color of petals.*—The blade of petals is approximately RHS 187-A or B when the flower first opens. A few hours after opening, the color of the blade of the petals lightens to RHS 187-B or C or 59-A or B. The color of the upper and lower petal surfaces are identical.

*Shape of individual petal.*—Broadly obovate. The petal apex is slightly wavering or undulating and the base and side margin is smooth.

*Texture of petal.*—Smooth, velvet-like.

*Color of petal claw.*—White, approximately RHS 155-A or B.

*Color of stamen tube.*—White, approximately RHS 155-A or B.

*Number of stamens and pistils.*—There are many stamens. Typically, there are 5 pistils but occasionally, only 3 or 4.

*Stigma.*—White, approximately RHS 155-A or B.

*Exposed portion of style.*—White, approximately R.H.S. 155-A or B.

*Pollen color.*—Light yellow, approximately RHS 12-B, C or D.

*Peduncle.*—The peduncle, the stalk of a single flower, is between about 0.5 and about one inch long, is stout, and has a color that is approximately RHS 147-B or C.

*Sepals.*—There are five sepals that are fused at the base to make a cup-like calyx, subtended by an epicalyx of between about 10 and about 18 bracts. The tips of the sepals are lanceolate. The sepals are typically between about 1.5 and about 2.5 inches long. Individual bracts are quite variable but typically range from between about one-half and about 2.5 inches long and between about one-eighth and about one-fourth inch wide. The color of the sepals and bracts range from between about RHS 147 A or B when the plant is in full sun and about RHS 191 A or B when shaded.

*Seed pods.*—Few seed pods are produced as the plant is mostly sterile. The color of old dry sepals surrounding the seed pod is approximately RHS 165-A or B. A young, immature seed pod is green, approximately RHS 151-A, soon after petal drop. The color changes to brown, approximately RHS 200-A or B, with age.

*Individual seeds.*—The seeds are more or less round, having a diameter of about ⅛ inch. The seeds are brown in color, approximately RHS 200-B or C.

I claim:

1. A new and distinct variety of a hardy hibiscus plant, substantially as illustrated and described.

* * * * *